United States Patent
Chassot et al.

(10) Patent No.: US 6,689,174 B2
(45) Date of Patent: Feb. 10, 2004

(54) N-BENZYL-P-PHENYLENEDIAMINE-DERIVATIVES CONTAINING COLORING AGENTS FOR KERATIN FIBRES AND NOVEL N-BENZYL-P-PHENYLENE-DIAMINE-DERIVATIVES

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 190 days.

(21) Appl. No.: 10/049,667

(22) PCT Filed: Mar. 19, 2001

(86) PCT No.: PCT/EP01/03121

§ 371 (c)(1),
(2), (4) Date: Jan. 1, 2002

(87) PCT Pub. No.: WO02/18318

PCT Pub. Date: Mar. 7, 2002

(65) Prior Publication Data

US 2002/0166181 A1 Nov. 14, 2002

(30) Foreign Application Priority Data

Aug. 31, 2000 (DE) .......................... 100 42 787

(51) Int. Cl.$^7$ ................................ A61K 7/13
(52) U.S. Cl. .................. 8/405; 8/406; 8/411; 8/412; 8/416; 544/180; 544/182; 548/561; 540/1
(58) Field of Search .................. 8/405, 406, 410, 8/411, 412, 416; 544/182, 180; 548/561; 540/1

(56) References Cited

U.S. PATENT DOCUMENTS 5,180,399 A * 1/1993 Grollier et al. ............... 8/405

FOREIGN PATENT DOCUMENTS

DE 34 32 214 A 3/1986
EP 0 024 660 A 3/1981

OTHER PUBLICATIONS

Chemical Abstracts, vol. 128, No. 23, Jun. 8, 1998 Columbus, Ohio, US, Abstract No.282671, Cherezova, E. N. et al: "Reaction of Dimethyl . . . " XP 205809–20–1 & Russ. J. Gen Chem. (1997), 67 (6), 932–935,1997.
Database Crossfire on Line! Beisteininformationssysteme XP 00216910 BRN 3282343 & Paal; Poller: J. Prakt. Chem. 1896, 272.
Chemical Abstracts, vol. 65, No. 5, Aug. 29, 1966. Columbus, Ohio, US, Abstract No. 7001F, G.N. Walker et al: "Synthesis of varified heterocyclic . . . " XP 002169309, RN 14015–50–0 & J. Med. Chem., BD 9, NR. 4, 1966, PP. 624–630.

* cited by examiner

Primary Examiner—Yogendra N. Gupta
Assistant Examiner—Eisa Elhilo
(74) Attorney, Agent, or Firm—Michael J. Striker

(57) ABSTRACT

Dyes, containing N-benzyl-p-phenylenediamine derivatives of the general formula (I) or their physiologically compatible salts,

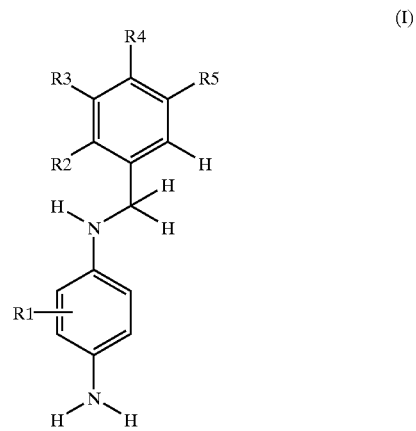

for keratin fibers, and new N-benzyl-p-phenylenediamine derivatives.

8 Claims, No Drawings

N-BENZYL-P-PHENYLENEDIAMINE-DERIVATIVES CONTAINING COLORING AGENTS FOR KERATIN FIBRES AND NOVEL N-BENZYL-P-PHENYLENE-DIAMINE-DERIVATIVES

The present invention relates to agents for oxidatively dyeing keratin fibers, especially human hair, on the basis of a combination of a developer and coupler, which contains N-benzyl-p-phenylenediamine derivatives as developer, as well as to new N-benzyl-p-phenylenediamine derivatives.

In the field of dyeing keratin fibers, especially of dyeing hair, oxidation dyes have achieved considerable importance. The dyeing results here from the reaction of certain developers with couplers in the presence of a suitable oxidizing agent. As developers, especially 2,5-diaminotoluene, 2,5-diaminophenylethyl alcohol, p-aminophenol and 1,4-diaminobenzene are used here, while as couplers, resorcinol, 4-chlororesorcinol, 1-naphthol, 3-aminophenol and derivatives of m-phenylenediamine, for example, are named.

Oxidation dyes, which are used for dyeing human hair, must satisfy numerous requirements, in addition to dyeing in the desired intensity. For example, the dyes must be safe from a toxicological and dermatological point of view and the hair dyeings achieved must have good light fastness, permanent waving fastness, acid resistance and crocking fastness. In any case, such dyeings must remain stable for a period of at least 4 to 6 weeks without the action of light, rubbing and chemical agents. In addition, it is necessary that a broad range of different color nuances can be produced by combining suitable developers and couplers.

From the German Offenlegungsschrift 34 32 214, agents, which contain a particular N-benzyl-p-phenylenediamine, such as N-benzyl-p-phenylenediamine, N4-benzyl-1,4-diamino-2-methylbenzene and 2-(((4-aminophenyl)amino)methyl)-4,6-dichloro-phenol, are already known for dyeing hair. However, these compounds do not fulfill the requirements, which must be met by dyes for oxidation dyes, in every respect. There is therefore a continuing need for further, suitable, new dyes.

It has now been found that, if N-benzyl-p-phenylenediamine derivatives of the general Formula (I) are used, intensive brown, blue and red color nuances are obtained.

The object of the present invention therefore is an agent for oxidatively dyeing keratin fibers, such as wool, fur, feathers or hair, especially human hair, on the basis of a combination of developer and coupler, which contains, as developer, at least one N-benzyl-p-phenylenediamine derivative of Formula (I),

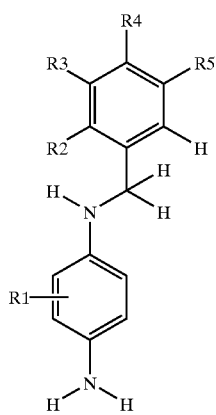

(I)

in which

R1 R1 is hydrogen, a ($C_1$–$C_4$) alkyl group or a hydroxy-($C_1$–$C_4$) alkyl group, R2 is hydrogen, a halogen atom (F, Cl, Br, I), a cyano group, a ($C_1$–$C_4$) alkoxy group, a hydroxy ($C_1$–$C_4$) alkoxy group, a ($C_1$–$C_6$) alkyl group, a ($C_1$–$C_4$) alkyl thioether group, a mercapto group, a nitro group, an amino group, a ($C_1$–$C_4$) alkylamino group, a di-($C_1$–$C_4$) alkylamino group, a di-(hydroxy-($C_1$–$C_4$)-alkyl) amino group, a (hydroxy-($C_1$–$C_4$)-alkyl) amino group, a trifluoromethane group, a —C(O)CH$_3$ group, a —C(O)CF$_3$ group, an —Si(CH$_3$)$_3$ group, a hydroxy-($C_1$–$C_4$) alkyl group, a dihydroxy-($C_3$–$C_4$) alkyl group or a morpholino group R3, R4 independently of one another are hydrogen, a halogen atom, a hydroxy group, a ($C_1$–$C_4$) alkoxy group, a hydroxy-($C_1$–$C_4$) alkoxy group, a ($C_1$–$C_6$) alkyl group, a ($C_1$–$C_4$) alkyl thioether group, a mercapto group, an amino group, a ($C_1$–$C_6$) alkylamino group, a di-($C_1$–$C_6$) alkylamino group, a di-(hydroxy-($C_1$–$C_4$)-alkylamino group, a hydroxy-($C_1$–$C_4$) alkylamino group, a trifluoromethane group, an acetamido group, a —C(O)CH$_3$ group, a —C(O)CF$_3$ group, an —Si(CH$_3$)$_3$ group, a hydroxy-($C_1$–$C_4$) alkyl group or a dihydroxy-($C_3$–$C_4$) alkyl group or R3 and R4 together form an —O—CH2—O— bridge and R5 is hydrogen, a hydroxy group or a ($C_1$–$C_6$) alkyl group, with the proviso that (i) at least one of the R2 to R5 groups is different from a hydrogen and (ii) R1 is not hydrogen or a (C1–C4) alkyl group when R2=R4=R5=hydrogen and R3=chlorine.

The following, for example, can be mentioned as examples of compounds of Formula (I): N-((2-aminophenyl)methyl)-1,4-diaminobenzene, N-((3-aminophenyl)-methyl)-1,4-diaminobenzene, N-((3-hydroxyphenyl)methyl)-1,4-diaminobenzene, N-((4-aminophenyl)methyl)-1,4-diaminobenzene, N-((4-hydroxyphenyl)methyl)-1,4-diaminobenzene, N-((2-(1-hydroxyethoxy)-phenyl)-methyl)-1,4-diaminobenzene, N-((2-methoxyphenyl)methyl)-1,4-diaminobenzene, N-((3-(1-hydroxyethoxy)-phenyl)methyl)-1,4diaminobezene, N-((3-methoxyphenyl)methyl)-1,4-diaminobenzene, N-((4-hydroxy-3,5-dimethyl-phenyl)methyl)-1,4-diaminobenzene, N-((4-(1-hydroxyethoxy)-phenyl)methyl)-1,4-diaminobenzene, N-((4-methoxyphenyl)methyl)-1,4-diaminobenzene, N-((2-(2-hydroxyethylamino)-phenyl)methyl)-1,4-diaminobenzene, N-((2-(bis-(2-hydroxyethyl)amino)-phenyl)methyl)-1,4-diaminobenzene, N-((2-dimethylamino-phenyl)methyl)-1,4-diaminobenzene, N-((2-pyrrolidino-phenyl)methyl)-1,4-diaminobenzene, N-((3-(2-hydroxyethylamino)-phenyl)methyl)-1,4-diaminobenzene, N-((3-(bis-(2-hydroxyethyl)amino)-phenyl)methyl)-1,4-diaminobenzene, N-((3-dimethyl-aminophenyl)methyl)-1,4-diaminobenzene, N-((3-pyrrolidino-phenyl)methyl)-1,4-diaminobenzene, N-((4-(2-hydroxyethylamino)-phenyl)methyl)-1,4-diaminobenzene, N-((4-(bis-(2-hydroxyethyl)amino)-phenyl)methyl)-1,4-diaminobenzene, N-((4-dimethylamino-phenyl)methyl)-1,4-diaminobenzene, N-((4-pyrrolidino-phenyl)methyl)-1,4-diaminobenzene, N-benzo[1,3]dioxol-5-ylmethyl-1,4-diaminobenzene, N-benzo[1,3]dioxol-6-ylmethyl-1,4-diaminobenzene, N-{2-[(4-amino-phenylamino)-methyl]-phenyl}-acetamide, N-{3-[(4-amino-phenylamino)-methyl]-phenyl}-acetamide, N-{4-[(4-amino-phenylamino)-methyl]-phenyl}-acetamide, N-((2,3-diaminophenyl)methyl)-1,4-diaminobenzene, N-((2,3-dihydroxyphenyl)

methyl)-1,4-diaminobenzene, N-((2,4-diaminophenyl) methyl)-1,4-diaminobenzene, N-((2,4-dihydroxyphenyl) methyl)-1,4-diaminobenzene, N-((2,5-diaminophenyl) methyl)-1,4-diaminobenzene, N-((2,5-dihydroxyphenyl) methyl)-1,4-diaminobenzene, N-((2,6-diaminophenyl) methyl)-1,4-diaminobenzene, N-((2,6-dihydroxyphenyl) methyl)-1,4-diaminobenzene, N-((2-hydroxy-3-aminophenyl)methyl)-1,4-diaminobenzene, N-((2-hydroxy-4-aminophenyl)methyl)-1,4-diaminobenzene, N-((2-hydroxy-5-aminophenyl)methyl)-1,4-diaminobenzene, N-((3-hydroxy-4-aminophenyl)methyl)-1,4-diaminobenzene, N-((3-hydroxy-5-aminophenyl)methyl)-1,4-diaminobenzene, N-((2-amino-3-hydroxyphenyl)methyl)-1,4-diaminobenzene, N-((2-amino-4-hydroxyphenyl)methyl)-1,4-diaminobenzene, $N^1$-((2-aminophenyl)methyl)-2-(2-hydroxyethyl)-1,4-diaminobenzene, $N^1$-((2-aminophenyl) methyl)-2-methyl-1,4-diaminobenzene, $N^1$-((3-aminophenyl)methyl)-2-(2-hydroxyethyl)-1,4-diaminobenzene, $N^1$-((3-aminophenyl)methyl)-2-methyl-1,4-diaminobenzene, $N^1$-((3-hydroxyphenyl)methyl)-2-(2-hydroxyethyl)-1,4-diaminobenzene, $N^1$-((3-hydroxyphenyl) methyl)-2-methyl-1,4-diaminobenzene, $N^1$-((4-aminophenyl)methyl)-2-(2-hydroxyethyl)-1,4-diaminobenzene, $N^1$-((4-aminophenyl)methyl)-2-methyl-1,4-diaminobenzene, $N^1$-((4-hydroxyphenyl)methyl)-2-(2-hydroxyethyl)-1,4-diaminobenzene, $N^1$-((4-hydroxyphenyl) methyl)-2-methyl-1,4-diaminobenzene, $N^4$-((2-aminophenyl)methyl)-2-(2-hydroxyethyl)-1,4-diaminobenzene, $N^4$-((2-aminophenyl)methyl)-2-methyl-1,4-diaminobenzene, $N^4$-((3-aminophenyl)methyl)-2-(2-hydroxyethyl)-1,4-diaminobenzene, $N^4$-((3-aminophenyl) methyl)-2-methyl-1,4-diaminobenzene, $N^4$-((3-hydroxyphenyl)methyl)-2-(2-hydroxyethyl)-1,4-diaminobenzene, $N^4$-((3-hydroxyphenyl)methyl)-2-methyl-1,4-diaminobenzene, $N^4$-((4-aminophenyl)methyl)-2-(2-hydroxyethyl)-1,4-diaminobenzene, $N^4$-((4-aminophenyl) methyl)-2-methyl-1,4-diaminobenzene, $N^4$-((4-hydroxyphenyl)methyl)-2-(2-hydroxyethyl)-1,4-diaminobenzene, $N^4$-((4-hydroxyphenyl)methyl)-2-methyl-1,4-diaminobenzene.

Compounds of Formula (I) are preferred in which (i) R1 and one of the groups R2 to R5 is hydrogen and/or
(ii) three of the R1 to R5 groups are hydrogen and the two remaining groups, independently of one another, represent hydrogen, a methoxy group, a hydroxy group or an amino group or, in the case of R3 and R4, jointly form an —O—CH2—O bridge, in which case R2 is not a hydroxy group and at least one of the R2 to R5 groups is not hydrogen.

The following N-benzyl-p-phenylenediamine derivatives of Formula (I) are particularly preferred: N-((3-hydroxyphenyl)methyl)-1,4-diaminobenzene; N-((4-aminophenyl)methyl)-1,4-diaminobenzene; N-((4-hydroxyphenyl)-methyl)-1,4-diaminobenzene; N-((2-methoxyphenyl)methyl)-1,4-diaminobenzene; N-((4-hydroxy-3,5-dimethyl-phenyl)methyl)-1,4-diaminobenzene; N-((4-(2-hydroxyethoxy)-phenyl)methyl)-1,4-diaminobenzene; N-benzo[1,3]dioxol-5-ylmethyl-1,4-diaminobenzene; N-{4-[(4-aminophenylamino)-methyl]-phenyl}-acetamide and N-((4-methoxyphenyl)-methyl)-1,4-diaminobenzene, as well as their physiologically compatible salts.

The compounds of Formula (I) can be used as free bases, as well as in the form of their physiologically compatible salts with inorganic or organic acids, such as hydrochloric acid, sulfuric acid, phosphoric acid, acetic acid, propionic acid, lactic acid or citric acid.

The N-benzyl-p-phenylenediamine derivatives of Formula (I) are contained in the inventive dyes in a total amount of about 0.005 to 20 percent by weight, amount of about 0.01 to 5 percent by weight and, in particular, of 0.1 to 2.5 percent by weight being preferred.

As coupler substances, preferably 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino toluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]-acetamide, 5-[(2-hydroxyethyl)amino]-2-methylphenol, 3-[(2-hydroxyethyl)amino]-phenol, 3-[(2-methoxyethyl)-amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxy-pyridine, 5-amino-4-chloro-2-methylphenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5pyrazolone, 5,6-dihydroxy-indole, 5,6-dihydroxy-indoline, 5-hydroxy-indole, 6-hydroxy-indole, 7-hydroxy-indole and 2,3-indolinedione come into consideration.

Although the advantageous properties of the compounds of formula (I) described here suggest that these be used as the only developer, it is, of course, also possible to use these compounds together with known developers, such as 1,4-diaminobenzene, 2,5-diaminotoluene, 2,5-diaminophenylethanol, 4-aminophenol and its derivatives (for example, 4-amino-3-methylphenol), 4,5-diamino-1-benzyl-1H-pyrazole, 4,5-diamino-1-((4'-methylbenzyl)-1H-pyrazole, 4,5-diamino-1H-pyrazole, 4,5-diamino-1-(4'-methoxybenzyl)-1H-pyrazole, 4,5-diamino-1-(3'-methoxybenzyl)-1H-pyrazole, 4,5-diamino-1-(4'-chlorobenzyl)-1H-pyrazole, 4,5-diamino-1-((4'-methylphenyl)-1H-pyrazole, 4,5-diamino-1-(4'-methoxyphenyl)-1H-pyrazole, 4,5-diamino-1-(3'-methoxyphenyl)-1H-pyrazole, 4,5-diamino-1-(4'-chlorophenyl)-1H-pyrazole, 4,5-diamino-1-(2'- hydroxyethyl)-1H-pyrazole, 4,5-diamino-1-methyl-1H-pyrazole, 4,5-diamino-1-ethyl-1H-pyrazole, 4-amino-1-((4-methoxyphenyl)methyl)-5-(methylamino)-1H-pyrazole, 4-amino-5-((2-hydroxyethyl)amino)-1-(phenylmethyl)-1H-pyrazole, 4,5-diamino-1-methyl-3-phenyl-1H-pyrazole, 4,5-diamino-1-(2-hydroxyethyl)-3-phenyl-1H-pyrazole, 4,5-diamino-1,3-dimethyl-1H-pyrazole, 4,5-diamino-3-methyl-1-phenyl-1H-pyrazole, 4,5-diamino-1-(1-isopropyl)-1H-pyrazole or tetraaminopyrimidines.

The couplers and the developers may be contained in the inventive dyes in each case individually or in admixture with one another, the total amount of the couplers and the developers in the inventive dye (based on the total amount of the dye) in each case being about 0.005 to 20 percent by weight, preferably about 0.01 to 5.0 percent by weight and particularly 0.1 to 2.5 percent by weight. The total amount of the combination of developer and coupler in the dye described here preferably is about 0.01 to 20 percent by weight, an amount of about 0.02 to 6 percent by weight and especially of 0.2 to 10 percent by weight being particularly preferred. The developers and couplers generally are used in approximately equimolar amounts; in this connection, however, it is not disadvantageous if the developers or the couplers are present in a certain excess (such as a ratio of coupler to developer of 1:2 to 1:0.5).

Furthermore, the inventive dye may additionally contain other dye components, such as 6-amino-2-methylphenol and 2-amino-5-methylphenol, as well as conventional direct dyes, for example, triphenylmethane dyes such as 4-[(4'-aminophenyl)-(4'-imino-2",5"-cyclohexadiene-1"-ylidene)-methyl]-2-methylaminobenzene monohydrochloride (C.I. 42 510) and 4-[(4'-amino-3'-methyl-phenyl)-(4"-imino-3"-methyl-2",5"-cyclohexadiene-1"-ylidene)-methyl]-2-methylaminobenzene monohydrochloride (C.I. 42 520), aromatic nitro dyes such as 4-(2'-hydroxyethyl)amino-nitrotoluene, 2-amino-4,6-dinitrophenol, 2-amino-5-(2'-hydroxyethyl)amino-nitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2amino-4-chloro-6-nitrophenol and 1-[(2'-ureidoethyl)amino-4-nitrobenzene, azo dyes such as the sodium salt of 6-[(4'-aminophenyl)azo]-5-hydroxy-naphthalene-1-sulfonic acid (C.I. 14 805) and dispersion dyes such as, for example, 1,4-diaminoanthraquinone and 1,4,5,8-tetraaminoanthraquinone. The aforementioned dye components may be contained in the inventive dyes in an amount of about 0.1 to 4 percent by weight.

Of course, if the couplers and developers as well as the other dye components are bases, they may also be used in the form of their physiologically compatible salts with organic or inorganic assets, such as hydrochloric acid or sulfuric acid, or, if they have aromatic OH groups, in the form of the salts with bases, such as alkali phenolates.

Moreover, the inventive dyes, if they are to be used to dye hair, may also contain other additives, conventionally used in cosmetic materials, for example, antioxidants, such as ascorbic acid, thioglycolic acid or sodium sulfite, as well as perfume oils, complexing agents, wetting agents, emulsifiers, thickeners and care materials.

The inventive dyes may be prepared in the form of a solution, especially an aqueous or aqueous alcoholic solution. However, the especially preferred form of the preparation is a cream, a gel or an emulsion. Its composition represents a mixture of the dye components with additives, which are usually employed for such preparations.

Conventional additives for solutions, creams, emulsions or gels are, for example, solvents such as water, low molecular weight aliphatic alcohols, such as ethanol, propanol or isopropanol, glycerin or glycols, such as 1,2-propylene glycol, wetting agents or emulsifiers of the anionic, cationic, amphoteric or nonionic class of surface active substances, such as fatty alcohol sulfates, ethoxylated fatty alcohol sulfates, alkyl sulfonates, alkylbenzene sulfonates, alkyltrimethylammonium salts, alkylbetaines, ethoxylated fatty alcohols, ethoxylated nonylphenoles, fatty acid alkanolamides and ethoxylated fatty acid esters, furthermore, thickeners such as higher molecular weight fatty alcohols, starch, cellulose derivatives, petroleum jelly, paraffin oil and fatty acids, as well as care materials, such as cationic resins, lanolin derivatives, cholesterol, pantothenic acid and betaine. The components mentioned are used in amounts, which a customary for such purposes; for example, the wetting agents and emulsifiers are used in concentrations of about 0.5 to 30 percent by weight, the thickness in an amount of about 0.1 to 25 percent by weight and the care materials in a concentration of about 0.1 to 5 percent by weight.

Depending on the composition, the inventive dye may be slightly acidic, neutral or alkaline. In particular, it has a pH of 6.5 to 11.5, the adjustment to a basic pH preferably being made with ammonia. However, organic amines, such as monoethanolamine and triethanolamine, or also inorganic bases, such as sodium hydroxide and potassium hydroxide may also be used. For adjusting the pH in the acidic range, inorganic organic acids, such as phosphoric acid, acetic acid, citric acid or tartaric acid comes into consideration.

If they are to be used for the oxidative dyeing of hair, the dyes, described above, are mixed immediately before use with an oxidizing agent and an amount of dye, sufficient for the treatment, is applied on the hair. Generally, about 50 to 200 gram of this mixture is applied, depending on the fullness of the latter. The ready-for-use oxidation dye, obtained upon mixing with the oxidizing agent, preferably has a pH of 6.5 to 11.5.

The following come into consideration as oxidizing agents for developing the hair dyeing: mainly hydrogen peroxide or its addition compounds with urea, melamine, sodium borate or sodium carbonate in the form of a 3 percent to 12 percent and preferably a 6 percent aqueous solution, also oxygen from the air. If a 6 percent hydrogen peroxide solution is used as oxidizing agent, the ratio by weight of hair dyeing agent to oxidizing agent is 5:1 to 1:2 and preferably 1:1. Larger amounts of oxidizing agent are used especially for higher concentrations of dye in the hair-dyeing agent or if greater bleaching of the hair is intended at the same time. The mixture is allowed to act on the hair for about 10 to 45 minutes and preferably for 30 minutes at 15° to 50° C. The hair is then rinsed with water and dried. Optionally, after the rinsing, the hair is washed with a shampoo and possibly rinsed with a weak organic acid, such as citric acid or tartaric acid. Subsequently, the hair is dried.

The inventive dye, containing N-benzyl-p-phenylenediamine derivatives of Formula (I) as developer, makes dyeings possible with excellent color fastness, especially as far as light fastness, wash fastness and crock fastness are concerned. With regard to the color properties, the inventive dyeing agent offers a wide range of different color nuances, ranging from blond, brown, purple and violet to blue and black color shades, depending on the nature and composition of the dye components. The shades of color are distinguished here especially by their color intensity. The very good dyeing properties of the dye of the present invention are furthermore shown by the fact that this material enables even grayish hair, which has not previously been damaged chemically, to be dyed without problems and with good covering power.

The inventive N-benzyl-p-phenylenediamine derivatives of Formula (I) can be synthesized using known methods, such as the methods described in the examples.

The N-benzyl-p-phenylenediamine derivatives of Formula (I) are readily soluble in water and make dyeings possible with a high color intensity and excellent color fastness, especially as far as light fastness, wash fastness and crock fastness are concerned. They furthermore have an excellent shelf life, especially as a component of the oxidation dyes, which are described here.

A further object of the present invention are new N-benzyl-p-phenylenediamine derivatives of Formula (I), in which R4 is not a nitro group, a methyl group, a hydroxy group, an amino group, a dimethylamino group, a bromine atom or a chlorine atom, when R1=R2=R3=R5=hydrogen, or their physiologically compatible, water-soluble salts.

The following examples are intended to explain the object of the invention in greater detail, without limiting the invention to these examples.

EXAMPLES

Example 1

Synthesis of N-benzyl-1,4-diaminobenzenes t-Butyl N-(4-aminophenyl) carbamate (0.031 gram, 0.15 mmoles) and 0.10 mmoles of the appropriate aldehyde are dissolved in 1,2-dichloroethane. Subsequently, 0.1 mL of an acetic acid solution (1 molar in 1,2-dichloroethane) and 0.06 g of NaBH(OAc)$_3$ (0.3 mmoles) are added and the reaction mixture is stirred for 5 to 15 hours at room temperature (20° to 25° C.). At the end of the reaction, the reaction mixture is poured into 10 mL of ethyl acetate and the organic phase is extracted with sodium hydrogen carbonate and then dried with magnesium sulfate. The solvent is evaporated in a rotary evaporator and the residue purified on silica gel with petroleum ether/ethyl acetate (9:1). The product, so obtained, is heated to 50° C. in 4 mL of ethanol and 1.5 mL of a 2.9 molar ethanolic hydrochloric acid solution. The precipitate is filtered off, washed twice with 1 mL of ethanol and then dried.

a. N-((3-hydroxyphenyl)methyl)-1,4-diaminobenzene hydrochloride
    Aldehyde used: 3-hydroxy-benzaldehyde
    Yield: 0.025 g (87% of the theoretical)
    Mass spectrum: MH+215(100)

b. N-((4-(2-hydroxyethoxy)-phenyl)methyl)-1,4-diaminobenzene hydrochloride
    Aldehyde used: 4-(2-hydroxyethoxy)-benzaldehyde
    Yield: 0.025 g (75% of the theoretical)
    Mass spectrum: MH+259(100)

c. N-{4-[(4-aminophenylamino)-methyl]-phenyl}-acetamide hydrochloride
    Aldehyde used: 4-acetamino-benzaldehyde
    Yield: 0.025 g (76% of the theoretical)
    Mass spectrum: MH+256(100)

d. 4-[(4-amino-phenylamino)-methyl]-2,6-dimethyl-phenol hydrochloride
    Aldehyde used: 2,6-dimethyl-4-hydroxy-benzaldehyde
    Yield: 0.025 g (79% of the theoretical)
    Mass spectrum: MH+243(100)

e. N-benzo[1,3]dioxol-5-ylmethyl-1,4-diamino-benzene hydrochloride
    Aldehyde used: 3,4-methylenedioxy-benzaldehyde
    Yield: 0.025 g (79% of the theoretical)
    Mass spectrum: MH+316(100)

f. N-((4-hydroxyphenyl)-methyl)-1,4-diaminobenzene
    Aldehyde used: 4-hydroxy-benzaldehyde
    Yield: 0.025 g (100% of the theoretical)
    Mass spectrum: MH+215(100)

g. N-((4-aminophenyl)-methyl)-1,4-diaminobenzene hydrochloride
    Aldehyde used: t-butyl N-(4-formyl-phenyl)carbamate
    Yield: 0.025 g (77% of the theoretical)
    Mass spectrum: MH+214(100)

h. N-(2-amino benzyl)-1,4-diaminobenzene hydrochloride
    Aldehyde used: 2-amino-benzaldehyde
    Yield: 0.025 g (77% of the theoretical)
    Mass spectrum: MH+214(100)

i. N-(2-methoxy-benzyl)-1,4-diaminobenzene hydrochloride
    Aldehyde used: 2-methoxy-benzaldehyde
    Yield: 0.025 g (83% of the theoretical)
    Mass spectrum: MH+229(100)

j. 4-[(4-aminophenylamino)-methyl]-1,2-dihydroxybenzene hydrochloride
    Aldehyde used: 3,4-dihydroxy-benzaldehyde
    Yield: 0.025 g (82% of the theoretical)
    Mass spectrum: MH+231(100)

k. 5-[(4-aminophenylamino)-methyl]-1,3-dihydroxybenzene hydrochloride
    Aldehyde used: 3,5-dihydroxy-benzaldehyde
    Yield: 0.025 g (82% of the theoretical)
    Mass spectrum: MH+231(100)

l. 5-(4-aminophenyl)aminomethyl-1,3-diaminobenzene hydrochloride
    Aldehyde used: 3,5-diamino-benzaldehyde
    Yield: 0.025 g (66% of the theoretical)
    Mass spectrum: MH+228(100)

m. N-((4-methoxyphenyl)methyl)-1,4-diaminobenzene hydrochloride
    Aldehyde used: 4-methoxy-benzaldehyde
    Yield: 0.025 g (83% of the theoretical)
    Mass spectrum: MH+229(100)

n. 4-amino-2-[(4-amino-phenylamino)-methyl]-phenol hydrochloride
    Aldehyde used: t-butyl N-(4-hydroxy-3-formyl-phenyl)-carbamate
    Yield: 0.025 g (73% of the theoretical)
    Mass spectrum: MH+230(100)

o. N-(4-pyrrolidine-1-yl-benzyl)-1,4-diaminobenzene
    Aldehyde used: 4-pyrrolidino-benzaldehyde
    Yield: 10 g (30% of the theoretical)

p. 2-[{4-[(4-amino-phenylamino)-methyl]-phenyl}-(2-hydroxyethyl)-amino]-ethanol hydrochloride
    Aldehyde used: 4-(bis(2-hydroxyethyl)amino)-benzaldehyde
    Yield: 0.025 g (60% of the theoretical)

q. N-(4-nitro-benzyl)-1,4-diaminobenzene hydrochloride
    Aldehyde used: 4-nitro-benzaldehyde
    Yield: 0.025 g (79% of the theoretical)
    Mass spectrum: MH+244(20)

r. N-(4-dimethylamino-benzyl)-1,4-diaminobenzene
    Aldehyde used: 4-dimethylamino-benzaldehyde
    Yield: 0.025 g (100% of the theoretical)
    Mass spectrum: MH+242(25)

s. 2-[(4-amino-phenylamino)-methyl]1,4-dihydroxybenzene hydrochloride
  Aldehyde used: 3,6-dihydroxy-benzaldehyde
  Yield: 0.025 g (82% of the theoretical)
  Mass spectrum: MH+231 (100)
t. N-(2,4-dinitro-benzyl)-1,4-diaminobenzene hydrochloride
  Aldehyde used: 2,4-dinitro-benzaldehyde
  Yield: 0.025 g (69% of the theoretical)
  Mass spectrum: MH+289(70)
u. N-(2-morpholino-4-yl-benzyl)-1,4-diaminobenzene hydrochloride
  Aldehyde used: 2-morpholino-benzaldehyde
  Yield: 0.025 g (70% of the theoretical)

Example 2
Synthesis of $N^1$-benzyl-1,4-diamino-2-methyl-benzenes and $N^4$-benzyl-1,4-diamino-2-methyl-benzenes A mixture of 0.033 g (0.15 mmoles) of t-butyl N-(4-amino-2-methyl-phenyl) carbamate and t-butyl N-(4-amino-3-methyl-phenyl) carbamate and 0.1 mmoles of the appropriate aldehyde is dissolved in 1,2-dichloroethane. Subsequently, 0.1 mL of an acetic acid solution (1 molar in 1,2-dichloroethane) and 0.06 g of $NaBH(OAc)_3$ (0.3 mmoles) are added and the reaction mixture is stirred for 5 to 15 hours at room temperature (20° to 25° C.). At the end of the reaction, the reaction mixture is poured into 10 mL of ethyl acetate and the organic phase is extracted with sodium hydrogen carbonate and then dried with magnesium sulfate. The solvent is evaporated in a rotary evaporator and the residue purified on silica gel with petroleum ether/ethyl acetate (9:1). The product, so obtained, is heated to 50° C. in 4 mL of ethanol and 1.5 mL of a 2.9 molar ethanolic hydrochloric acid solution. The precipitate is filtered off, washed twice with 1 mL of ethanol and then dried.

a. $N^1$-(4-amino-benzyl)-2-methyl-1,4-diaminobenzene hydrochloride and $N^1$-(4-amino-benzyl)-3-methyl-1,4-diaminobenzene hydrochloride
  Aldehyde used: t-butyl N-(4-formyl-phenyl)-carbamate
  Yield: 0.025 g (37% of the theoretical)
  Mass spectrum: MH+228(40)
b. 4-amino-2-[(4-amino-2-methyl-phenylamino)-methyl]-phenol hydrochloride and 4-amino-2-[(4-amino-3-methyl-phenylamino)-methyl]-phenol hydrochloride
  Aldehyde used: t-butyl N-(4-hydroxy-3-formyl-phenyl)-carbamate
  Yield: 0.025 g (35% of the theoretical)
  Mass spectrum: MH+244(100)
c. $N^1$-(2-methoxy-benzyl)-2-methyl-1,4-diaminobenzene hydrochloride and $N^1$-(2-methoxy-benzyl)-3-methyl-1,4-diaminobenzene hydrochloride
  Aldehyde used: 2-methoxy-benzaldehyde
  Yield: 0.025 g (39% of the theoretical)
  Mass spectrum: MH+243(100)
d. $N^1$-(3-amino-benzyl)-2-methyl-1,4-diaminobenzene hydrochloride and $N^1$-(3-amino-benzyl)-3-methyl-1,4-diaminobenzene hydrochloride
  Aldehyde used: 3-amino-benzaldehyde
  Yield: 0.025 g (37% of the theoretical)
  Mass spectrum: MH+228(100)
e. 3-[(4-amino-2-methyl-phenylamino)-methyl]-phenol hydrochloride and 3-[(4-amino-3-methyl-phenylamino)-methyl]-phenol hydrochloride
  Aldehyde used: 3-hydroxybenzaldehyde
  Yield: 0.025 g (41% of the theoretical)
  Mass spectrum: MH+229(100)
f. $N^1$-(4-methoxy-benzyl)-2-methyl-1,4-diaminobenzene and $N^1$-(4-methoxy-benzyl)-3-methyl-1,4diaminobenzene hydrochloride
  Aldehyde used: 4-methoxy-benzaldehyde
  Yield: 0.025 g (39% of the theoretical)
  Mass spectrum: MH+243(100)
g. 5-(4-amino-2-methyl-phenyl)aminomethyl-1,3-diaminobenzene hydrochloride and 5-(4-amino-3-methyl-phenyl)aminomethyl-1,3-diaminobenzene hydrochloride
  Aldehyde used: 3,5-diaminobenzaldehyde
  Yield: 0.025 g (32% of the theoretical)
  Mass spectrum: MH+243(100)
h. 2-{4-[(4-amino-2-methyl-phenylamino)-methyl]-phenoxy}-ethanol hydrochloride and 2-{4-[(4-amino-3-methyl-phenylamino)-methyl]-phenoxy}-ethanol hydrochloride
  Aldehyde used: 4-(2-hydroxyethoxy)-benzaldehyde
  Yield: 0.025 g (36% of the theoretical)
  Mass spectrum: MH+273(100)
i. 2-[{4-[(4-amino-2-methyl-phenylamino)-methyl]-phenyl}-(2-hydroxyethyl)-amino]-ethanol and 2-[{4-[(4-amino-3-methyl-phenylamino)-methyl]-phenyl}-(2-hydroxyethyl)-amino]-ethanol
  Aldehyde used: 4-(bis-(2-hydroxyethyl)-amino)-benzaldehyde
  Yield: 10 g (16% of the theoretical)
j. $N^1$-(2-amino-benzyl)-2-methyl-1,4-diaminobenzene hydrochloride and $N^1$-(2-amino-benzyl)-3-methyl-1,4-diaminobenzene hydrochloride
  Aldehyde used: 2-amino-benzaldehyde
  Yield: 0.025 g (37% of the theoretical)
k. 2-[(4-amino-2-methyl-phenylamino)-methyl]-1,4-dihydroxybenzene hydrochloride and 2-[(4-amino-3-methyl-phenylamino)-methyl]-1,4-dihydroxybenzene hydrochloride
  Aldehyde used: 3,6-dihydroxybenzaldehyde
  Yield: 0.025 g (39% of the theoretical)
  Mass spectrum: MH+245(100)
l. 2-methyl-$N^1$-(4-nitro-benzyl)-1,4-diaminobenzene hydrochloride and 3-methyl-$N^1$-(4-nitro-benzyl)-1,4-diaminobenzene hydrochloride
  Aldehyde used: 4-nitro-benzaldehyde
  Yield: 0.025 g (37% of the theoretical)
  Mass spectrum: MH+258(100)
m. 2-{4-[(4-amino-2-methyl-phenylamino)-methyl]-phenoxy}-ethanol hydrochloride and 2-{4-[(4-amino-3-methyl-phenylamino)-methyl]-phenoxy}-ethanol hydrochloride
  Aldehyde used: 4-(2-hydroxy-ethoxy)-benzaldehyde
  Yield: 0.025 g (36% of the theoretical)
  Mass spectrum: MH+273(100)
n. N-{4-[(4-amino-2-methyl-phenylamino)-methyl]-phenyl}-acetamide hydrochloride and N-{4-[(4-amino-3-methyl-phenylamino)-methyl]-phenyl}-acetamide hydrochloride
  Aldehyde used: 4-acetamido-benzaldehyde
  Yield: 0.025 g (36% of the theoretical)
  Mass spectrum: MH+270(100)
o. 4-[(4-amino-2-methyl-phenylamino)-methyl]-phenol hydrochloride and 4-[(4-amino-3-methyl-phenylamino)-methyl]-phenol hydrochloride
  Aldehyde used: 4-hydroxy-benzaldehyde
  Yield: 0.025 g (41% of the theoretical)
  Mass spectrum: MH+229(100)

p. 2-methyl-N$^1$-(2-morpholine-4-yl-benzyl)-1,4-diaminobenzene hydrochloride and 3-methyl-N$^1$-(2-morpholine-4-yl-benzyl)-1,4-diaminobenzene hydrochloride Aldehyde used: 2-morpholino-benzaldehyde
Yield: 0.025 g (30% of the theoretical)

q. N$^1$-(4-dimethylamino-benzyl)-2-methyl-1,4-diaminobenzene and N$^1$-(4-dimethylamino-benzyl)-3-methyl-1,4-diaminobenzene Aldehyde used: 4-dimethylamino-benzaldehyde
Yield: 0.025 g (48% of the theoretical)
Mass spectrum: MH−254(100)

Example 3

Synthesis of N$^1$-benzyl-1,4-diamino-2-(2-hydroxyethyl)-benzenes and N$^4$-benzyl-1,4-diamino-2-(2-hydroxyethyl)benzenes A mixture of 0.038 g (0.15 mmoles) of t-butyl N-(4-amino-2(2-hydroxyethyl)-phenyl) carbamate and N-(4-amino-3-(2-hydroxyethyl)-phenyl) carbamate and 0.1 mmoles of the appropriate aldehyde are dissolved in 1,2-dichloroethane. Subsequently, 0.1 mL of an acetic acid solution (1 molar in 1,2-dichloroethane) and 0.06 g of NaBH(OAc)$_3$ (0.3 mmoles) are added and the reaction mixture is stirred for 5 to 15 hours at room temperature (20° to 25° C.). At the end of the reaction, the reaction mixture is poured into 10 mL of ethyl acetate and the organic phase is extracted with sodium hydrogen carbonate and then dried with magnesium sulfate. The solvent is evaporated in a rotary evaporator and the residue purified on silica gel with petroleum ether/ethyl acetate (9:1). The product, so obtained, is heated to 50° C. in 4 mL of ethanol and 1.5 mL of a 2.9 molar ethanolic hydrochloric acid solution. The precipitate is filtered off, washed twice with 1 mL of ethanol and then dried.

a. 2-[5-amino-2-(4-nitro-benzylamino)-phenyl]-ethanol hydrochloride and 2-[6-amino-3-(4-nitro-benzylamino)-phenyl]-ethanol hydrochloride Aldehyde used: 4-nitro-benzaldehyde
Yield: 0.025 g (34% of the theoretical)
Mass spectrum: MH+288(100)

b. 2-[5-amino-2-(3-amino-benzylamino)-phenyl]-ethanol hydrochloride and 2-[6-amino-3-(3-amino-benzylamino)-phenyl]-ethanol hydrochloride Aldehyde used: 3-amino-benzaldehyde
Yield: 0.025 g (34% of the theoretical)
Mass spectrum: MH+258(100)

c. 2-[5-amino-2-(4-amino-benzylamino)-phenyl]-ethanol hydrochloride and 2-[6-amino-3-(4-amino-benzylamino)-phenyl]-ethanol hydrochloride Aldehyde used: t-butyl N-(4-formyl-phenyl)-carbamate
Yield: 0.025 g (34% of the theoretical)
Mass spectrum: MH+258(50)

d. 2-[5-amino-2-(4-methoxy-benzylamino)-phenyl]-ethanol hydrochloride and 2-[6-amino-3-(4-methoxy-benzylamino)-phenyl]-ethanol hydrochloride Aldehyde used: 4-methoxy-benzaldehyde
Yield: 0.025 g (35% of the theoretical)
Mass spectrum: MH+273(100)

e. 2-[(4-{[4-amino-2-(2-hydroxyethyl)-phenylamino]-methyl}-phenyl)-(2-hydroxyethyl)-amino]-ethanol and 2-[(4-{[4-amino-3-(2-hydroxyethyl-phenylamino]-methyl}-phenyl)-(2-hydroxyethyl)-amino]-ethanol Aldehyde used: 4-bis(2-hydroxyethyl)amino-benzaldehyde
Yield: 15 g (25% of the theoretical)

f. 2-[5-amino-2-(2-methoxy-benzylamino)-phenyl]-ethanol hydrochloride and 2-[6-amino-3-(2-methoxy-benzylamino)-phenyl]-ethanol hydrochloride Aldehyde used: 2-methoxy-benzaldehyde
Yield: 0.025 g (36% of the theoretical)
Mass spectrum: MH+273(100)

g. 2-[5-amino-2-(2-amino-benzylamino)-phenyl]-ethanol hydrochloride and 2-[6-amino-3-(2-amino-benzylamino)-phenyl]-ethanol hydrochloride Aldehyde used: 2-amino-benzaldehyde
Yield: 0.025 g (34% of the theoretical)
Mass spectrum: MH+258(100)

h. 2-{[4-amino-2-(2-hydroxyethyl)-phenylamino]-methyl}-1,4-dihydroxy-benzene hydrochloride and 2-{[4-amino-3-(2-hydroxyethyl)-phenylamino]-methyl}-1,4-dihydroxy-benzene hydrochloride Aldehyde used: 3,6-dihydroxy-benzaldehyde
Yield: 0.025 g (36% of the theoretical)
Mass spectrum: MH+275(100)

i. 4-amino-2-{[4-amino-2-(2-hydroxyethyl)-phenylamino]-methyl}-phenol hydrochloride and 4-amino-2-{[4-amino-3-(2-hydroxyethyl)-phenylamino]-methyl}-phenol hydrochloride Aldehyde used: t-butyl N-(4-hydroxy-3-formyl-phenyl)-carbamate
Yield: 0.025 g (32% of the theoretical)
Mass spectrum: MH+274(100)

j. 2-[5-amino-2-(2-morpholine-4-yl-benzylamino)-phenyl]-ethanol hydrochloride and 2-[6-amino-3-(2-morpholine-4-yl-benzylamino)-phenyl]-ethanol hydrochloride Aldehyde used: 2-morpholino-benzaldehyde
Yield: 0.025 g (28% of the theoretical)

k. 2-[5-amino-2-(4-dimethylamino-benzylamino)-phenyl]-ethanol and 2-[6-amino-3-(4-dimethylamino-benzylamino)-phenyl]-ethanol Aldehyde used: 4-dimethylamino-benzaldehyde
Yield: 0.025 g (42% of the theoretical)

l. 2-[2-amino-5-(3,5-diamino-benzylamino)-phenyl]-ethanol hydrochloride and 2-[5-amino-2-(3,5-diamino-benzylamino)-phenyl]-ethanol hydrochloride Aldehyde used: 3,5-diamino-benzaldehyde
Yield: 0.025 g (29% of the theoretical)
Mass spectrum: MH+273(100)

Examples 4 to 53

Hair Dyes

Hair dye solutions of the following composition are prepared:

| | | |
|---|---|---|
| 1.25 mmoles | developer substance of Formula (I) of Table 1 | |
| 1.25 mmoles | coupler of Table 1 | |
| 1.0 g | potassium oleate (8% aqueous solution) | |
| 1.0 g | ammonia (22% aqueous solution) | |
| 1.0 g | ethanol | |
| 0.3 g | ascorbic acid | |
| ad 100.0 g | water | |

Immediately before use, the above dye solution (50 g) is mixed with 50 g of a 6 percent aqueous hydrogen peroxide solution. Subsequently, the mixture is applied on bleached hair. After a period of action of 30 minutes at 40° C., the hair is rinsed with water, washed with a conventional, commercial shampoo and dried. The resulting dye means are summarized in Table 1.

TABLE 1

| Example No. | Developer Formula (I) | Coupler I. 1,3-dihydroxy-benzene | Coupler II. 1,3-diamino-4-(2-hydroxy-ethoxy)-benzene sulfate | Coupler III. 5-amino-2-methyl-phenol | Coupler IV. 1-naphthol |
|---|---|---|---|---|---|
| 4. | of Example 1a | brown | dark blue | purple | blue |
| 5. | of Example 1b | dark blond | dark blue | purple | blue |
| 6. | of Example 1c | dark blond | dark blue | purple | blue |
| 7. | of Example 1d | gray | blue | purple | blue |
| 8. | of Example 1e | dark blond | blue | purple | blue |
| 9. | of Example 1f | dark blond | blue | purple | blue |
| 10. | of Example 1g | dark blond | blue | purple | blue |
| 11. | of Example 1h | medium blond | blue | purple | blue |
| 12 | of Example 1i | light blond | blue | purple | blue-gray |
| 13. | of Example 1j | blond | blue | purple | blue-gray |
| 14. | of Example 1k | dark blond | blue | purple | blue-gray |
| 15. | of Example 1l | brown | blue | purple-blue | blue-gray |
| 16. | of Example 1m | dark blond | blue | dark purple | blue |
| 17. | of Example 1n | light blond | blue-gray | purple | purple |
| 18. | of Example 1o | light blond | blue | purple | blue |
| 19. | of Example 1p | medium blond | blue | purple | blue |
| 20. | of Example 1q | dark blond | blue | purple | violet |
| 21. | of Example 1r | light blond | blue | purple | violet |
| 22. | of Example 1s | light blond | blue | purple | violet |
| 23. | of Example 1t | light blond | blue | purple | light violet |
| 24. | of Example 1u | light blond | blue | purple | light violet |
| 25. | of Example 2a | medium blond | blue | purple | violet |
| 26. | of Example 2b | blond | blue | purple | violet |
| 27. | of Example 2c | medium blond | blue | purple | violet |
| 28. | of Example 2d | medium blond | blue | purple | blue |
| 29. | of Example 2e | medium blond | blue | purple | violet |
| 30. | of Example 2f | medium blond | blue | purple | violet |
| 31. | of Example 2g | blond | blue | purple | violet |
| 32. | of Example 2h | light blond | blue | purple | violet |
| 33. | of Example 2i | light blond | blue | purple | violet |
| 34. | of Example 2j | light blond | blue | purple | violet |
| 35. | of Example 2k | light blond | blue | purple | gray |
| 36. | of Example 2l | blond | blue | purple | gray-violet |
| 37. | of Example 2m | light blond | blue | purple | violet |
| 38. | of Example 2n | dark blond | blue | purple | violet |

TABLE 1-continued

| Example No. | Developer Formula (I) | Coupler I. 1,3-dihydroxy-benzene | Coupler II. 1,3-diamino-4-(2-hydroxy-ethoxy)-benzene sulfate | Coupler III. 5-amino-2-methyl-phenol | IV. 1-naphthol |
|---|---|---|---|---|---|
| 39. | of Example 2o | light blond | blue | purple | violet |
| 40. | of Example 2p | light blond | blue | purple | violet |
| 41. | of Example 2q | light blond | blue | purple | violet |
| 42. | of Example 3a | medium blond | blue | purple | blue-gray |
| 43. | of Example 3b | light blond | blue | purple | blue |
| 44. | of Example 3c | dark blond | blue | purple | violet |
| 45. | of Example 3d | light blond | blue | purple | light blue |
| 46. | of Example 3e | light blond | blue | purple | violet |
| 47. | of Example 3f | light blond | blue | purple | violet |
| 48. | of Example 3g | light blond | blue | purple | light blue |
| 49. | of Example 3h | light blond | blue | purple | violet |
| 50. | of Example 3i | light blond | blue | purple | violet |
| 51. | of Example 3j | light blond | blue | purple | light blue |
| 52. | of Example 3k | light blond | blue | purple | violet |
| 53. | of Example 3l | light blond | blue | purple | violet |

Examples 54 to 123

Hair Dyes

Hair dye solutions of the following composition are prepared:

| | | |
|---|---|---|
| X g | N-(benzyl)-1,4-diamino-benzene (developer E1 to E7 of Formula (I) of Table 2) | |
| U g | Developer E8 to E15 of Table 2 | |
| Y g | Coupler K11 to K36 of Table 4 | |
| Z g | direct dye D1 to D3 of Table 3 | |
| 10.0 g | potassium oleate (8% aqueous solution) | |
| 10.0 g | ammonia (22% aqueous solution) | |
| 10.0 g | ethanol | |
| 0.3 g | ascorbic acid | |
| ad 100.0 g | water | |

Immediately before use, the above dye solution (30 g) is mixed with a 30 g of a 6 percent aqueous hydrogen peroxide solution. Subsequently, the mixture is applied on bleached hair. After a period of action of 30 minutes at 40° C., the hair is rinsed with water, washed with a conventional, commercial shampoo and dried. The dyeing results are summarized in Table 5.

Examples 124 to 165

Hair Dyes

Creamy dye carrier compositions of the following composition are prepared:

| | | |
|---|---|---|
| X g | N-(benzyl)-1,4-diamino-benzene (developer substance E1 to E7 of Formula (I) of Table 2) | |
| U g | Developer E8 to E15 of Table 2 | |
| Y g | Coupler K11 to K36 of Table 4 | |
| Z g | direct dye D2 of Table 3 | |
| 15.0 g | cetyl alcohol | |
| 0.3 g | ascorbic acid | |
| 3.5 g | sodium lauryl alcohol diglycol ether sulfate, 28% aqueous solution | |
| 3.0 g | ammonia, 22% aqueous solution | |
| 0.3 g | sodium sulfite, anlydrous | |
| ad 100.0 g | water | |

Immediately before use, the above dye cream (30 g) is mixed with 30 g of a 6 percent aqueous hydrogen peroxide solution. Subsequently, the mixture is applied on hair. After a period of action of 30 minutes at 40° C., the hair is reduced with water, washed with a conventional, commercial shampoo and dried. The dyeing results are summarized in Table 6.

TABLE 2

| | Developer |
|---|---|
| E1 | N-((3-hydroxyphenyl)methyl)-1,4-diaminobenzene hydrochloride |
| E2 | N-((4-aminophenyl)methyl)-1,4-diaminobenzene hydrochloride |
| E3 | N-((4-(2-hydroxyethoxy)-phenyl)methyl)-1,4-diaminobenzene hydrochloride |
| E4 | N-((4-methoxyphenyl)methyl)-1,4-diaminobenzene hydrochloride |
| E5 | N-{4-[(4-amino-phenylamino)-methyl]-phenyl}-acetamide hydrochloride |
| E6 | N-((4-hydroxyphenyl)-methyl)-1,4-diaminobenzene |
| E7 | N-benzo[1,3]dioxol-5-ylmethyl-1,4-diaminobenzene hydrochloride |
| E8 | 1,4-diaminobenzene |
| E9 | 2,5-diamino-phenylethanol sulfate |
| E10 | 3-methyl-4-amino-phenol |
| E11 | 4-amino-2-aminomethyl-phenol-dihydrochloride |
| E12 | 4-amino-phenol |
| E13 | N,N-bis(2'-hydroxyethyl)-p-phenylenediamine sulfate |
| E14 | 4,5-diamino-1-(2'-hydroxyethyl)-pyrazole sulfate |
| E15 | 2,5-diaminotoluene sulfate |

TABLE 3

| | Direct Dyes |
|---|---|
| D1 | 2,6-diamino-3-((pyridine-3-yl)azo)pyridine |
| D2 | 6-chloro-2-ethylamino-4-nitrophenol |
| D3 | 2-amino-6-chloro-4-nitrophenol |

TABLE 4

| | Coupler |
|---|---|
| K11 | 1,3-diaminobenzene |
| K12 | 2-amino-4-(2'-hydroxyethyl)amino-anisole sulfate |
| K13 | 1,3-diamino-4-(2'-hydroxyethoxy)benzene sulfate |
| K14 | 2,4-diamino-5-fluoro-toluene sulfate |
| K15 | 3-amino-2-methylamino-6-methoxy-pyridine |
| K16 | 3,5-diamino-2,6-dimethoxy-pyridine-dihydrochloride |
| K17 | 2,4-diamino-5-ethoxy-toluene sulfate |
| K18 | N-(3-dimethylamino)phenylurea |
| K19 | 1,3-bis(2,4-diaminophenoxy)propane-tetrahydrochloride |
| K21 | 3-amino-phenol |
| K22 | 5-amino-2-methyl-phenol |
| K23 | 3-amino-2-chloro-6-methyl-phenol |
| K24 | 5-amino-4-fluoro-2-methyl-phenol sulfate |
| K25 | 1-naphthol |
| K26 | 1-acetoxy-2-methyl-naphthalene |
| K31 | 1,3-dihydroxy-benzene |
| K32 | 2-methyl-1,3-dihydroxy-benzene |
| K33 | 1-chloro-2,4-dihydroxy-benzene |
| K34 | 4-(2'-hydroxyethyl)amino-1,2-methylenedioxybenzene hydrochloride |
| K35 | 3,4-methylenedioxy-phenol |
| K36 | 2-amino-5-methyl-phenol |

TABLE 5

Hair Dyes

| Example No. | 54 | 55 | 56 | 57 |
|---|---|---|---|---|
| Dye | (amount of dye in gram) | | | |
| E1 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | 0.30 | 0.30 |

TABLE 5-continued

Hair Dyes

| | | | | | | |
|---|---|---|---|---|---|---|
| K26 | | | 0.35 | | | |
| Dyeing Result | reddish brown | reddish brown | reddish brown | reddish brown | | |

| Example No. | 58 | 59 | 60 | 61 | 62 | 63 |
|---|---|---|---|---|---|---|
| Dye | (amount of dye in grams) | | | | | |
| E1 | 0.35 | 0.25 | 0.3 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 64 | 65 | 66 | 67 |
|---|---|---|---|---|
| Dye | (amount of dye in grams) | | | |
| E2 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

| Example No. | 68 | 169 | 70 | 71 | 72 | 73 |
|---|---|---|---|---|---|---|
| Dye | (amount of dye in grams) | | | | | |
| E1 | 0.35 | 0.25 | 0.3 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 74 | 75 | 76 | 77 |
|---|---|---|---|---|
| Dye | (amount of dye in grams) | | | |
| E3 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

TABLE 5-continued

Hair Dyes

| Example No. | 78 | 79 | 80 | 81 | 82 | 83 |
|---|---|---|---|---|---|---|
| Dye | (amount of dye in grams) | | | | | |
| E3 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 84 | 85 | 86 | 87 |
|---|---|---|---|---|
| Dye | (amount of dye in grams) | | | |
| E4 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

| Example No. | 88 | 89 | 90 | 91 | 92 | 93 |
|---|---|---|---|---|---|---|
| Dye | (amount of dye in grams) | | | | | |
| E4 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 94 | 95 | 96 | 97 |
|---|---|---|---|---|
| Dye | (amount of dye in grams) | | | |
| E5 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

| Example No. | 98 | 99 | 100 | 101 | 102 | 103 |
|---|---|---|---|---|---|---|
| Dye | (amount of dye in grams) | | | | | |
| E5 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 104 | 105 | 106 | 107 |
|---|---|---|---|---|
| Dye | (amount of dye in grams) | | | |
| E6 | 0.20 | 0.15 | 0.15 | 0.15 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

| Example No. | 108 | 109 | 110 | 111 | 112 | 113 |
|---|---|---|---|---|---|---|
| Dye | (amount of dye in grams) | | | | | |
| E6 | 0.25 | 0.20 | 0.25 | 0.05 | 0.05 | 0.10 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing Result | blond | blond | blond | blond | blond | blond |

| Example No. | 114 | 115 | 116 | 117 |
|---|---|---|---|---|
| Dye | (amount of dye in grams) | | | |
| E7 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyeing Result | reddish brown | reddish brown | reddish brown | reddish brown |

| Example No. | 118 | 119 | 120 | 121 | 122 | 123 |
|---|---|---|---|---|---|---|
| Dye | (amount of dye in grams) | | | | | |
| E7 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |

TABLE 5-continued

Hair Dyes

| K22 | | 0.05 | | | | |
|---|---|---|---|---|---|---|
| K23 | | | 0.05 | 0.10 | 0.10 | 0.10 |
| Dyeing Result | blond | blond | blond | blond | blond | blond |

TABLE 6

Hair Dyeing Agents

| Example No. | 124 | 125 | 126 | 127 | 128 | 129 |
|---|---|---|---|---|---|---|
| Dye | (amount of dye in grams) | | | | | |
| E1 | 1.80 | 1.80 | 1.80 | 0.70 | 0.70 | 0.70 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 130 | 131 | 132 | 133 | 134 | 135 |
| Dye | (amount of dye in grams) | | | | | |
| E2 | 2.00 | 2.00 | 2.00 | 0.80 | 0.80 | 0.80 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 136 | 137 | 138 | 139 | 140 | 141 |
| Dye | (amount of dye in grams) | | | | | |
| E3 | 2.00 | 2.00 | 2.00 | 0.80 | 0.80 | 0.80 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 142 | 143 | 144 | 145 | 146 | 147 |
| Dye | (amount of dye in grams) | | | | | |
| E4 | 1.90 | 1.90 | 1.90 | 0.70 | 0.75 | 0.75 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 148 | 149 | 150 | 151 | 152 | 153 |
| Dye | (amount of dye in grams) | | | | | |
| E5 | 2.0 | 2.0 | 2.0 | 0.8 | 0.80 | 0.80 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 154 | 155 | 156 | 157 | 158 | 159 |
| Dye | (amount of dye in grams) | | | | | |
| E6 | 3.00 | 3.00 | 3.00 | 1.20 | 1.20 | 1.20 |
| K12 | | | | 0.10 | 0.10 | 0.10 |

TABLE 6-continued

Hair Dyeing Agents

| K13 | 1.10 | 1.10 | 1.10 | | | |
|---|---|---|---|---|---|---|
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |
| Example No. | 160 | 161 | 162 | 163 | 164 | 165 |
| Dye | (amount of dye in grams) | | | | | |
| E7 | 2.00 | 2.00 | 2.00 | 0.80 | 0.80 | 0.80 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing Result | black | black | black | brown | brown | brown |

Unless stated otherwise, all percentages in the present application are percentages by weight.

What is claimed is:

1. N-benzyl-p-phenylenediamine derivatives of the general Formula (I) or their physiologically compatible, water-soluble salts

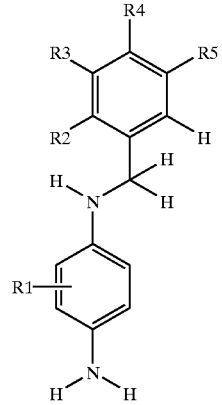

(I)

in which

R1 R1 is hydrogen, a ($C_1$–$C_4$) alkyl group or a hydroxy-($C_1$–$C_4$) alkyl group, R2 is hydrogen, a halogen atom (F, Cl, Br, I), a cyano group, a ($C_1$–$C_4$) alkoxy group, a hydroxy ($C_1$–$C_4$) alkoxy group, a ($C_1$–$C_6$) alkyl group, a ($C_1$–$C_4$) alkyl thioether group, a mercapto group, a nitro group, an amino group, a ($C_1$–$C_4$) alkylamino group, a di-($C_1$–$C_4$) alkylamino group, a di-(hydroxy-($C_1$–$C_4$)-alkyl) amino group, a (hydroxy-($C_1$–$C_4$)-alkyl) amino group, a trifluoromethane group, a —C(O)CH$_3$ group, a —C(O)CF$_3$ group, an —Si(CH$_3$)$_3$ group, a hydroxy-($C_1$–$C_4$) alkyl group, a dihydroxy-($C_3$–$C_4$) alkyl group or a morpholino group R3, R4 independently of one another are hydrogen, a halogen atom, a hydroxy group, a ($C_1$–$C_4$) alkoxy group, a hydroxy-($C_1$–$C_4$) alkoxy group, a ($C_1$–$C_6$) alkyl group, a ($C_1$–$C_4$) alkyl thioether group, a mercapto group, an amino group, a ($C_1$–$C_6$) alkylamino group, a di-($C_1$–$C_6$) alkylamino group, a di-(hydroxy-($C_1$–$C_4$)-alkyl)amino group, a hydroxy-($C_1$–$C_4$) alkylamino group, a trifluoromethane group, an acetamido group, a —C(O)CH$_3$ group, a —C(O)CF$_3$ group, an —Si(CH$_3$)$_3$ group, a hydroxy-(C$_1$–C$_4$) alkyl group or a dihydroxy-(C$_3$–C$_4$) alkyl group or R3 and R4 together form an —O—CH2—O— bridge and R5 is hydrogen, a hydroxy group or a (C$_1$–C$_6$) alkyl group, with the proviso that (i) at least one of the R2 to R5 groups is different from a hydrogen and (ii) R1 is not hydrogen or a (C$_1$–C$_4$) alkyl group when R2=R4 R5=hydrogen and R3=chlorine and ((iii) R4 is not a nitro group, a methyl group, a hydroxy group, an amino group, a dimethylamino group, a bromine atom or a chlorine atom when R1=R2=R3= R5=hydrogen.

2. Compounds of Formula (I) are preferred in which (i) R1 and one of the groups R2 to R5 is hydrogen and/or (ii) three of the R1 to R5 groups are hydrogen and the two remaining groups, independently of one another, represent hydrogen, a methoxy group, a hydroxy group or an amino group or, in the case of R3 and R4, jointly form an —O—CH2—O bridge, in which case R2 is not a hydroxy group and at least one of the R2 to R5 groups is not hydrogen; and/or (iii) four of the R1 to R5 groups are hydrogen and the fifth group is a methoxy group, a hydroxyethoxy group, a hydroxy group or an amino group, R2 not being a hydroxy group and at least one of the R2 to R5 groups being different from hydrogen.

3. An agent for dyeing keratin fibers based on a combination of developer and coupler, wherein, as developer, at least one N-benzyl-p-phenylenediamine derivative of Formula (I) or its physiologically compatible, water soluble salt is contained

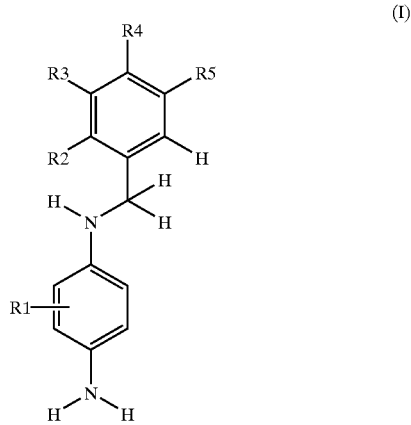

(I)

in which

R1 R1 is hydrogen, a (C$_1$–C$_4$) alkyl group or a hydroxy-(C$_1$–C$_4$) alkyl group R2 is hydrogen, a halogen atom (F, Cl, Br, I), a cyano group, a (C$_1$–C$_4$) alkoxy group, a hydroxy (C$_1$–C$_4$) alkoxy group, a (C$_1$–C$_6$) alkyl group, a (C$_1$–C$_4$) alkyl thioether group, a mercapto group, a nitro group, an amino group, a (C$_1$–C$_4$) alkylamino group, a di-(C$_1$–C$_4$) alkylamino group, a di-(hydroxy-(C$_1$–C$_4$)-alkyl) amino group, a (hydroxy-(C$_1$–C$_4$)-alkyl) amino group, a trifluoromethane group, a —C(O)CH$_3$ group, a —C(O)CF$_3$ group, an —Si(C$_{13}$)$_3$ group, a hydroxy-(C$_1$–C$_4$) alkyl group, a dihydroxy-(C$_3$–C$_4$) alkyl group or a morpholino group R3, R4 independently of one another are hydrogen, a halogen atom, a hydroxy group, a (C$_1$–C$_4$) alkoxy group, a hydroxy-(C$_1$–C$_4$) alkoxy group, a (C$_4$–C$_6$) alkyl group, a (C$_1$–C$_4$) alkyl thioether group, a mercapto group, an amino group, a (C$_1$–C$_6$) alkylamino group, a di-(C$_1$–C$_6$) alkylamino group, a di-(hydroxy-(C$_1$–C$_4$)-alkyl) amino group, a hydroxy-(C$_1$–C$_4$) alkylamino group, a trifluoromethane group, an acetamido group, a —C(O)CH$_3$ group, a —C(O)CF$_3$ group, an —Si(CH$_3$)$_3$ group, a hydroxy-(C$_1$–C$_4$) alkyl group or a dihydroxy-(C$_3$–C$_4$) alkyl group or R3 and R4 together form an —O—CH2—O— bridge and R5 is hydrogen, a hydroxy group or a (C$_1$–C$_6$) alkyl group, with the proviso that (i) at least one of the R2 to R5 groups is different from a hydrogen and (ii) R1 is not hydrogen or a (C$_1$–C$_4$) alkyl group when R2=R4=R5=hydrogen and R3=chlorine.

4. The agent of claim 3, wherein (i) R1 and one of the groups R2 to R5 is hydrogen and/or (ii) three of the R1 to R5 groups are hydrogen and the two remaining groups, independently of one another, represent hydrogen, or methoxy group, a hydroxy group or an amino group or, in the case of R3 and R4, jointly form an —O—CH2—O bridge, in which case R2 is not a hydroxy group and at least one of the R2 to R5 groups is not hydrogen; and/or (iii) four of the R1 to R5 groups are hydrogen and the fifth group is a methoxy group, a hydroxyethoxy group, a hydroxy group or an amino group, R2 not being a hydroxy group and at least one of the R2 to R5 groups being different from hydrogen, with the proviso that at least one of the R2 to R5 groups is different from hydrogen.

5. The agent of claim 3, wherein the compound of Formula (I) is selected from the group comprising: N-((3-hydroxyphenyl)methyl)-1,4-diaminobenzene; N-((4-aminophenyl)methyl)-1,4-diaminobenzene; N-((4-hydroxyphenyl)-methyl)-1,4-diaminobenzene; N-((2-methoxyphenyl)methyl)-1,4-diaminobenzene; N-((4-hydroxy-3,5-dimethyl-phenyl)methyl)-1,4-diaminobenzene; N-((4-(2-hydroxyethoxy)-phenyl)methyl)-1,4-diaminobenzene; N-benzo[1,3]dioxol-5-ylmethyl-1,4-diaminobenzene; N-{4-[(4-aminophenylamino)-methyl]-phenyl}-acetamide and N-((4-methoxyphenyl)-methyl)-1,4-diaminobenzene, as well as their physiologically compatible salts.

6. The agent of claim 3, wherein the N-benzyl-p-phenylenediamine derivative of Formula (I) is contained in an amount of 0.005 to 20 percent by weight.

7. The agent of claim 3, wherein the agent has a pH of 6.5 to 11.5.

8. The agent of claim 3, wherein the coupler is selected from the group comprising 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 2,4-diamino-1,5-di (2-hydroxyethoxy)-benzene, 1-(2-aminoethoxy)-2,4-diaminobenzene, 2-amino-1-(2-hydroxyethoxy)-4- methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino toluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]-acetamide, 5-[(2-hydroxyethyl)amino]-2-methylphenol, 3-[(2-hydroxyethyl)amino]-phenol, 3-[(2-methoxyethyl)-amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diamino-benzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indoline, 5-hydroxy-indole, 6-hydroxy-indole, 7-hydroxy-indole and 2,3-indolinedione.

* * * * *